(12) United States Patent
Baynham (10) Patent No.: US 10,238,499 B2
(45) Date of Patent: Mar. 26, 2019

(54) BILATERAL CLAMPING SPACER

(71) Applicant: Atlas Spine, Inc., Jupiter, FL (US)

(72) Inventor: Matthew G. Baynham, Jupiter, FL (US)

(73) Assignee: Atlas Spine, Inc., Jupiter, FL (US)

( * ) Notice: Subject to any disclaimer, the term of this patent is extended or adjusted under 35 U.S.C. 154(b) by 641 days.

(21) Appl. No.: 14/657,442

(22) Filed: Mar. 13, 2015

(65) Prior Publication Data

US 2015/0282940 A1 Oct. 8, 2015

Related U.S. Application Data

(60) Provisional application No. 61/953,621, filed on Mar. 14, 2014.

(51) Int. Cl.
*A61F 2/44* (2006.01)
*A61F 2/30* (2006.01)

(52) U.S. Cl.
CPC ............ *A61F 2/442* (2013.01); *A61F 2/4465* (2013.01); *A61F 2002/3051* (2013.01); *A61F 2002/30166* (2013.01); *A61F 2002/30281* (2013.01); *A61F 2002/30332* (2013.01); *A61F 2002/30484* (2013.01); *A61F 2002/30485* (2013.01); *A61F 2002/30509* (2013.01); *A61F 2002/30515* (2013.01); *A61F 2002/30517* (2013.01); *A61F 2002/30578* (2013.01); *A61F 2002/30599* (2013.01); *A61F 2002/4475* (2013.01); *A61F 2220/0016* (2013.01); *A61F 2230/0084* (2013.01)

(58) Field of Classification Search
CPC ............... A61B 17/7059; A61F 2/4455–2/447
See application file for complete search history.

(56) References Cited

U.S. PATENT DOCUMENTS

| | | |
|---|---|---|
| 5,658,336 A | 8/1997 | Pisharodi |
| 5,893,890 A | 4/1999 | Pisharodi |
| 6,214,050 B1 | 4/2001 | Huene |
| 6,309,421 B1 | 10/2001 | Pisharodi |
| 6,558,424 B2 | 5/2003 | Thalgott |
| 6,746,484 B1 | 6/2004 | Liu et al. |
| 6,773,460 B2 | 8/2004 | Jackson |
| 7,195,643 B2 | 3/2007 | Jackson |
| 7,214,243 B2 | 5/2007 | Taylor |
| 7,819,921 B2 | 10/2010 | Grotz |

(Continued)

*Primary Examiner* — Olivia C Chang
(74) *Attorney, Agent, or Firm* — McHale & Slavin, P.A.

(57) ABSTRACT

A spinal implant for stabilizing two adjacent vertebrae having a damaged disc therebetween is assembled in situ. The implant consists of a bone tray, an anchor, a retainer plate, a retainer, and mounting screws. The bone tray bone tray is elliptical shaped and includes an open top side and an open bottom side, the top side and the bottom side adapted to engage the end plates of adjacent vertebrae, respectively, the bone tray having a sidewall connecting the top side and the bottom side, the sidewall having an bore therethrough. The retainer is slidably extending through the bore whereby the distractor anchor is adapted to be inserted between adjacent vertebrae and the retainer extends through the retainer plate. The retainer plate is secured to the vertebrae body by mounting screws. A driver, not shown, is adapted to rotate the retainer which engages the distractor anchor to engage the bone tray.

6 Claims, 6 Drawing Sheets

(56) References Cited

U.S. PATENT DOCUMENTS

| | | |
|---|---|---|
| 7,850,733 B2 | 12/2010 | Baynham et al. |
| 8,470,039 B2 * | 6/2013 | Blain ................ A61B 17/7059 623/17.11 |
| 2005/0065605 A1 | 3/2005 | Jackson |
| 2005/0065606 A1 | 3/2005 | Jackson |
| 2007/0270968 A1 | 11/2007 | Baynham et al. |
| 2008/0140207 A1 * | 6/2008 | Olmos .................... A61F 2/447 623/17.16 |
| 2008/0269758 A1 | 10/2008 | Baynham et al. |
| 2009/0024217 A1 | 1/2009 | Levy et al. |
| 2009/0265007 A1 | 10/2009 | Colleran |
| 2009/0292361 A1 | 11/2009 | Lopez |

* cited by examiner

FIG 8

BILATERAL CLAMPING SPACER

PRIORITY CLAIM

In accordance with 37 C.F.R. 1.76, a claim of priority is included in an Application Data Sheet filed concurrently herewith. Accordingly, the present invention claims priority to U.S. Provisional Patent Application No. 61/953,621, entitled "BILATERAL CLAMPING SPACER", filed Mar. 14, 2014. The contents of the above referenced application is incorporated herein by reference in its entirety.

FIELD OF THE INVENTION

This invention relates to the field of orthopedic surgery and to spinal implants.

BACKGROUND OF THE INVENTION

The spinal disc is the natural shock absorber located between all vertebrae. In the event it becomes traumatized through injury or degenerates through age or disease, the intervertebral space is reduced through compression, and the relative movement of adjacent vertebrae causes pain. The surgical approach to this problem is to relieve the compression, stabilize the adjacent vertebrae and provide for a natural fusing of the vertebrae into one unit.

There are many spinal implants used to stabilize two adjacent vertebrae to prevent relative movement until the vertebrae are fused together by bony ingrowth through and around the implant. Generally these implants are in three groups, i.e., bone plates, pedicle screw/rod constructs and spinal cages. The bone plates span the intervertebral space and are affixed to the two adjacent vertebrae anteriorly by bone screws. Pedicle screw/rod constructs span the vertebral bodies posteriorly and are often connected with cross-links.

The spinal cages are inserted between the adjacent vertebrae and are usually seated into the end plates of the adjacent vertebrae. To gain access to the intervertebral space, a site is prepared by removing a portion or all of the spinal disc. A wedge shaped distractor is inserted into the site to gradually separate the adjacent vertebrae until the desired intervertebral space is achieved and cut into the end plates of the adjacent vertebrae. Once the site is prepared, the distractor is removed and the spinal implant is inserted into the disc space. The spinal implant may be packed with bone growth material, bone chips, a combination of both, or other material.

SUMMARY OF THE INVENTION

Disclosed is a spinal implant for fusing adjacent vertebrae. The implant consists of a bone tray, a distractor anchor, a retainer plate, a retainer screw, and mounting screws. The bone tray is elliptical shaped and includes an open top side and an open bottom side, the top side and the bottom side adapted to engage the end plates of adjacent vertebrae, respectively, the bone tray having a sidewall connecting the top side and the bottom side, the sidewall having a bore therethrough. The retainer is slidably extending through the bore, whereby the distractor anchor is adapted to be inserted between adjacent vertebrae and the retainer extends through the retainer plate. The retainer plate is secured to the vertebrae body by mounting screws. A driver, not shown, is adapted to rotate the retainer, which engages the distractor anchor to engage the bone tray. The bone tray is adapted to slide and contact the distractor anchor.

Therefore, it is an objective of this invention to provide a spinal implant to be assembled in situ.

It is another objective of this invention to provide an implantable distractor for site preparation and establishment of proper intervertebral space.

It is a still further objective of this invention to provide a retainer to attach the distractor and the bone tray together.

Other objectives and advantages of this invention will become apparent from the following description taken in conjunction with the accompanying drawings wherein are set forth, by way of illustration and example, certain embodiments of this invention. The drawings constitute a part of this specification and include exemplary embodiments of the present invention and illustrate various objects and features thereof.

DETAILED DESCRIPTION OF THE INVENTION

Figure 1:
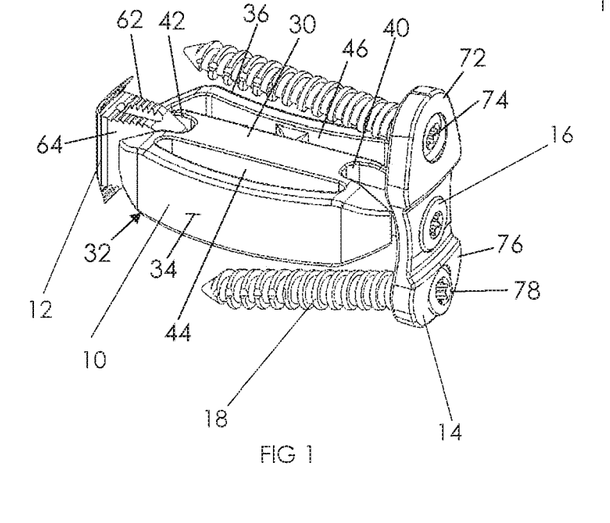
FIG. 1 is a perspective view of the implant.
Figure 2:
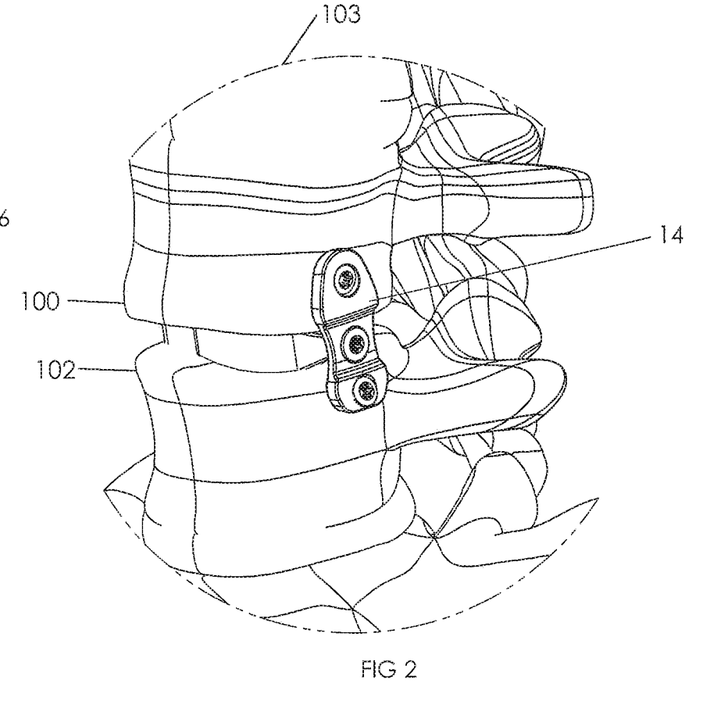
FIG. 2 is a pictorial view of the implant mounted in the spine.

Referring to FIGS. 1 and 2, disclosed is a spinal implant for fusing adjacent vertebrae using a retainer plate. The implant consists of a bone tray 10, a distractor anchor 12, a retainer plate 14, a retainer screw 16, and mounting screws 18. The bone tray 10 includes a top side 30 and a bottom side 32 adapted to engage the disc plates 100, 102 of a vertebrae. The bone tray 10 includes a top side 30 and a bottom side 32 adapted to engage the disc plates 100, 102 of a vertebrae 103. The bone tray 10 includes a first side wall 34, shown with a convex shape, and a second side wall 36, depicted with a concave shape. The first and second side walls 34, 36 have an equal thickness measured between the top side 30 and bottom side 32. A proximal end of said first sidewall 34 is separated from the second sidewall 36 by receptacle 40. A distal end of said first sidewall 34 is separated from the second sidewall 36 by receptacle 42. The bone tray 10 further includes a first aperture 44 extending from the top side to the bottom side for receipt of bone growth material. A second aperture 46 extends from the top side to the bottom side, also for receipt of bone growth material. The apertures 44 and 46 may traverse the length of the bone tray, or be placed in cross sections between side walls 34 and 36, all of which is designed to allow spatial implanting of bone growth material.

Figure 10:
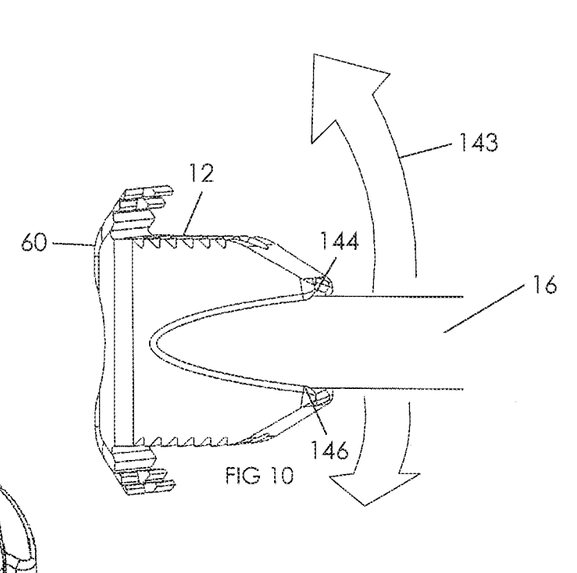
FIG. 10 is a rear view of the anchor.
Figures 11, 12, 13:
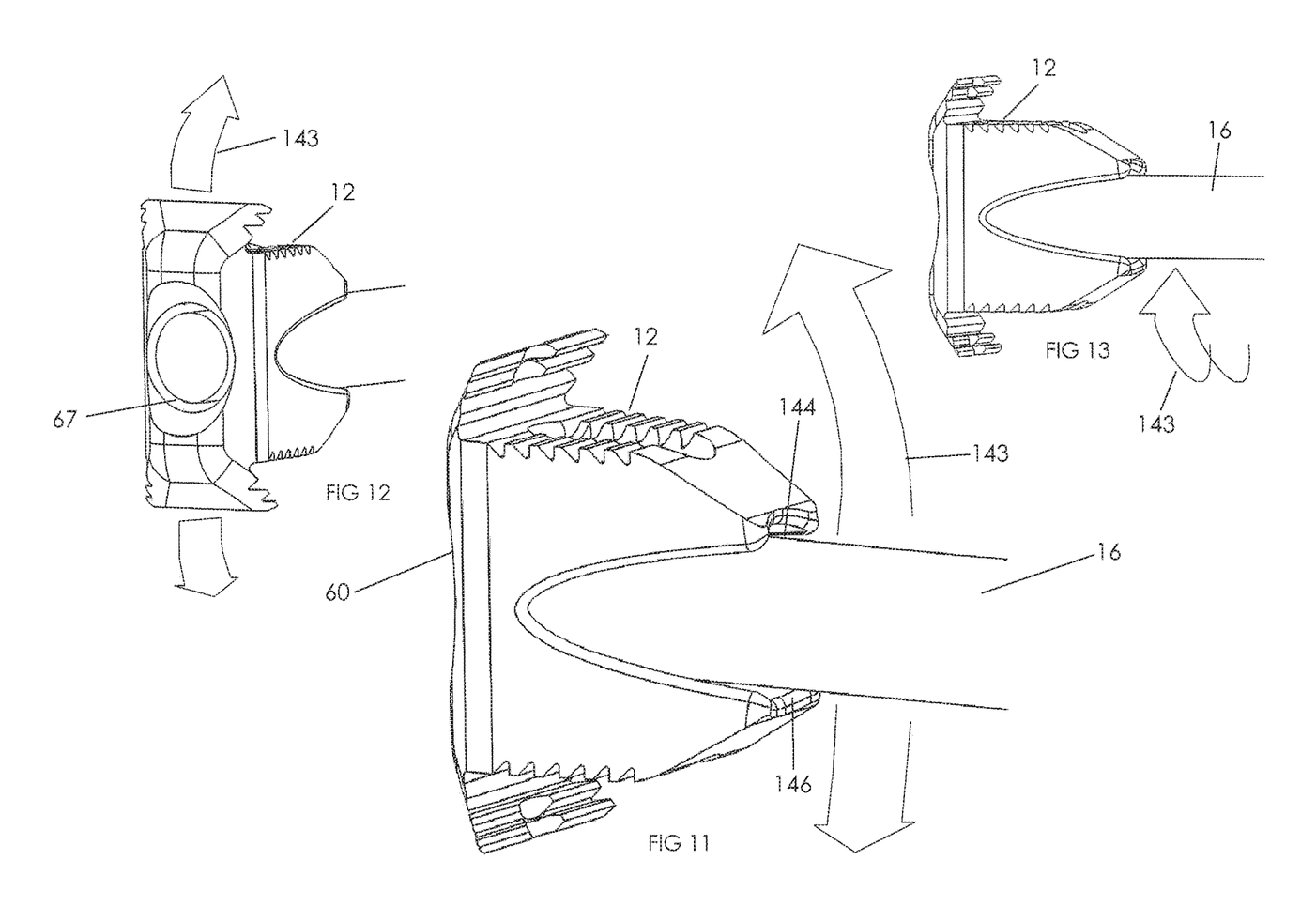
FIG. 11 is a side view of the anchor.
FIG. 12 is a front view of the anchor.
FIG. 13 is a side view of the anchor.

Distractor anchor 12 has a first sloped wall 50 and a second sloped wall 52, constructed and arranged to align with the receptacle 42. The distractor anchor 12 includes a aperture 56 formed along a bottom of the distractor where the sloped walls 50, 52 meet. An anchor member 60 is positioned along a top portion of the distractor 12, either formed integral as depicted or as a separate element as detailed later in this specification. The distractor 12 is further defined by opposing side walls 62 and 64, defining a width that is greater than the thickness of the bone tray 10 as measured between upper wall 30 and lower wall 32. The width of the distractor 12 allows the distractor to be inserted through an opening less than the thickness of the bone tray 10. Upon insertion, the distractor 12 is rotated as depicted by the directional arrow 143 shown in FIG. 10 for placement into the receptacle 42.

Retainer member 14 is associated with the proximal end of the bone tray 10. The retainer member 14 has a centrally disposed aperture 68 for receipt of a retainer 16 insertable through aperture 68. The retainer member 14 having a threaded end 67 for coupling to the aperture 56. The retainer member 14 has, in one embodiment, a first wing member 72 for receipt of mounting screw 74 and second wing member 76 placed in line with the first wing member 72 for receipt of mounting screw 78. In operation, the distractor 12 can be inserted in a position parallel to the bone tray and then rotated into a position wherein the side walls 62, 64 have a width greater than the thickness of the bone tray 10, as measured between the upper surface 30 and lower surface 32, providing an engagement surface for attaching to the spinal discs.

Figure 3:
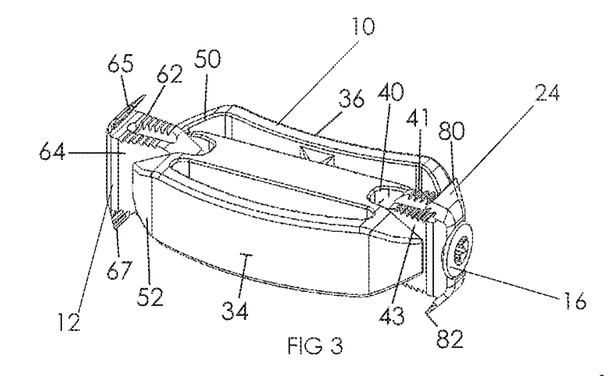
FIG. 3 is a perspective view of an alternative embodiment of the implant.

Referring now to FIG. 3, retainer 24 in this embodiment can form a mirror image of a distractor anchor 12. In this embodiment, the retainer 24 includes a retainer 16 for coupling to the first distractor 12; retainer 24 having an enlarged barb 80 extending outward from a first side wall of the retainer 24, and a second barb 82 extending outward from a second side wall of the retainer 24. The retainer 24 having a first sloped wall 41 and a second sloped wall 43 for engaging the receptacle 40. Similarly, distractor 12 is illustrated with a barb 65 extending outward from the first side wall of the distractor 12, and a barb 67 extending outward from the second side wall of the distractor 12.

Figures 4, 5, 6, 7:
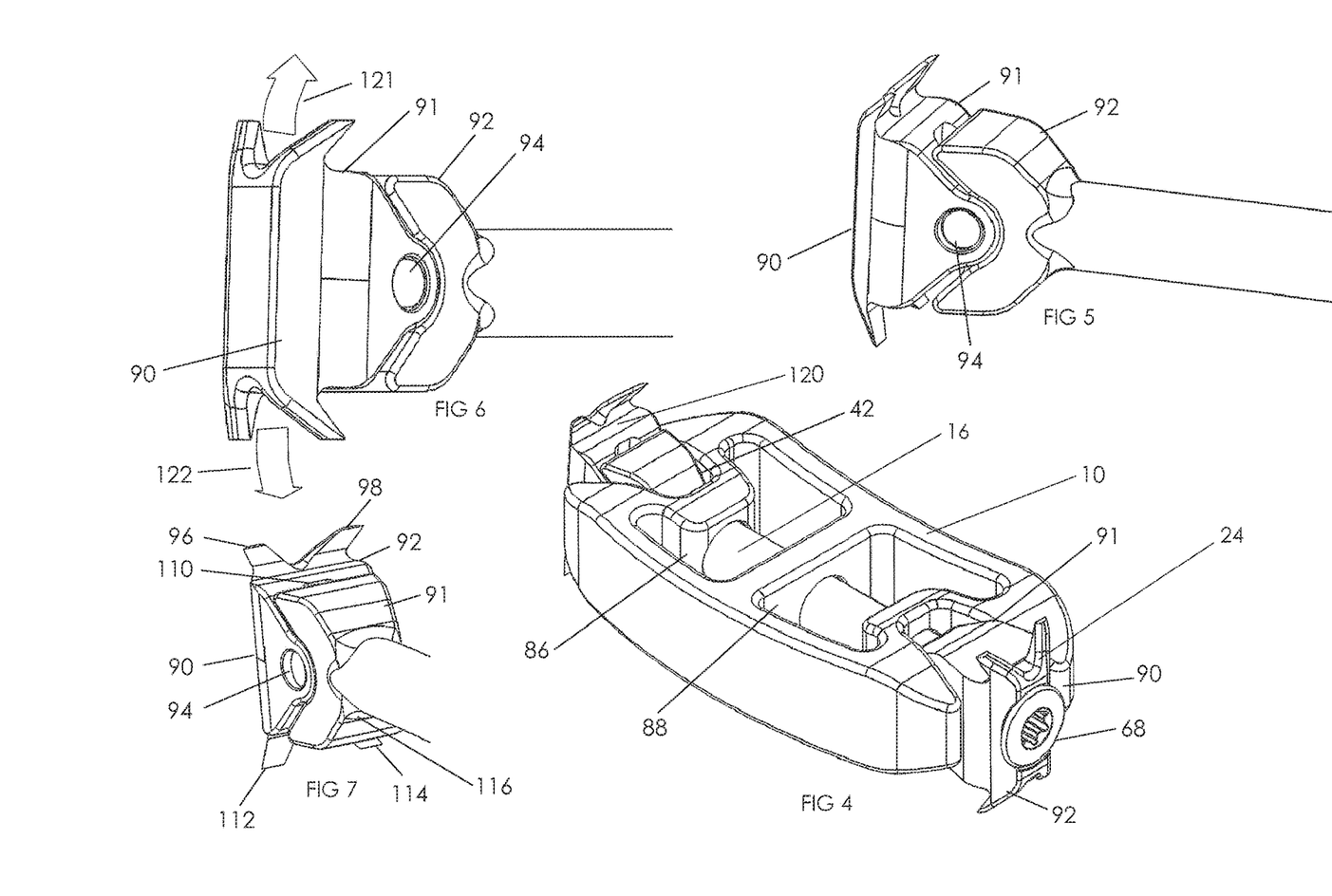
FIG. 4 is a perspective view of an alternative embodiment of the implant.
FIG. 5 is a rear view of the anchor.
FIG. 6 is a front view of the anchor.
FIG. 7 is a enlarged view of an engagement tab of the anchor.

Referring now to FIG. 4, set forth is a bone tray 10 depicted with distractor anchor 120 placed within the receptacle 42. In this embodiment, the bone tray has square shaped receptacles 86, 88 for receipt of bone growth material. The retainer member 90 in this embodiment includes an anchor member 91 that is pivotally connected to the distractor anchor 120 by use of a pivot pin 94. The distractor anchor 120 and retainer member 90 in this embodiment are similar in which distractor anchor 120 has dual barbs 96 and 98 located along an upper edge 110, and barbs 112 and 114 located along a lower edge 116. The retainer screw 68 is sized so that the head of the screw is rotatably secured to the retainer member 90 and the distractor anchor 120. Illustrated in FIG. 6, the anchor member 90 may articulate up or down, as depicted by the arrows 121 and 122, so as to allow the barbs 96, 98 on one end and barbs 112, 114 on the opposite end to engage bone, allowing the distractor anchor 120 to engage the V-slot 42 as an angle that provides even pressure to the spinal discs used for engagement.

Figure 8:
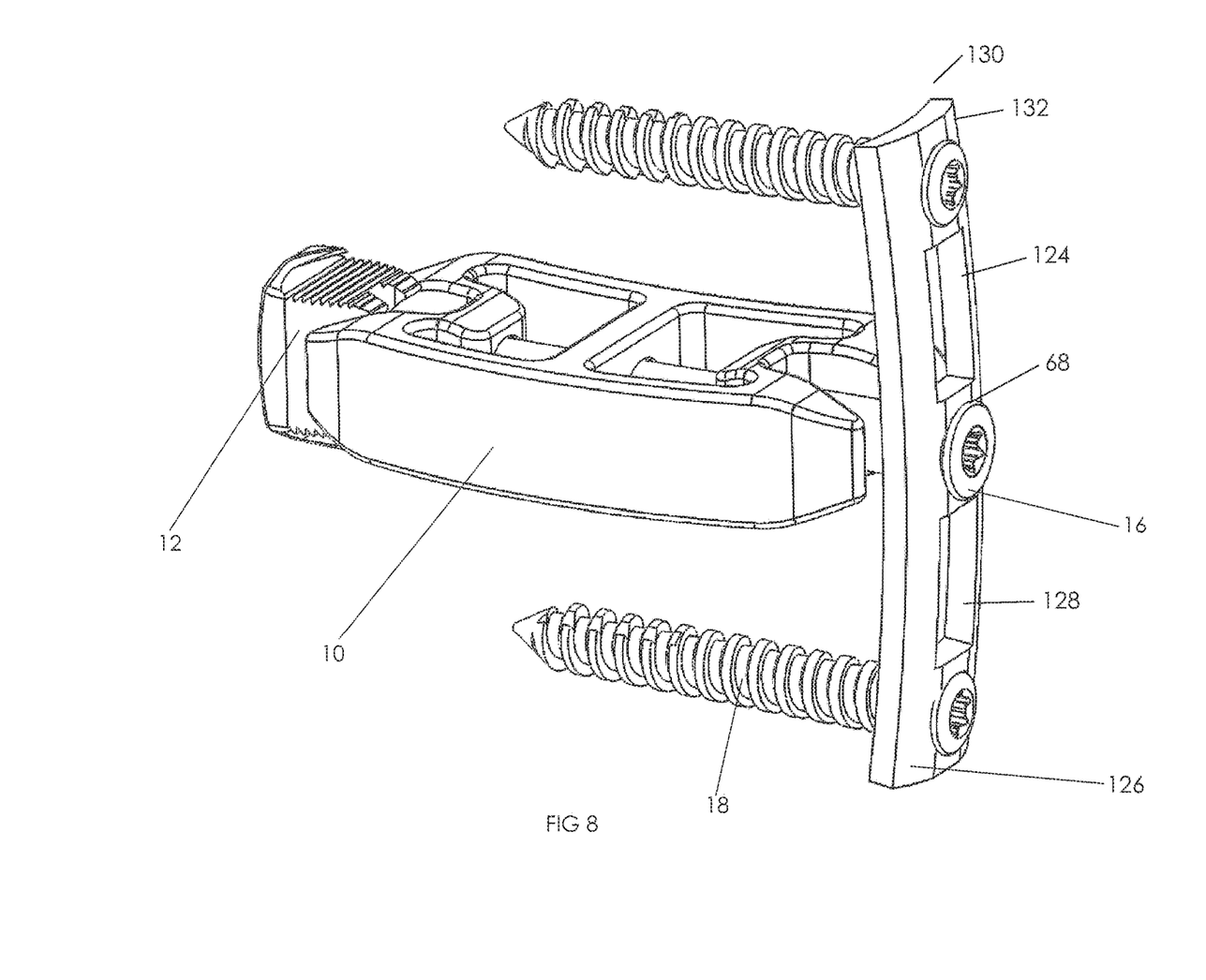
FIG. 8 is a perspective view of an alternative embodiment of the implant.
Figure 9:
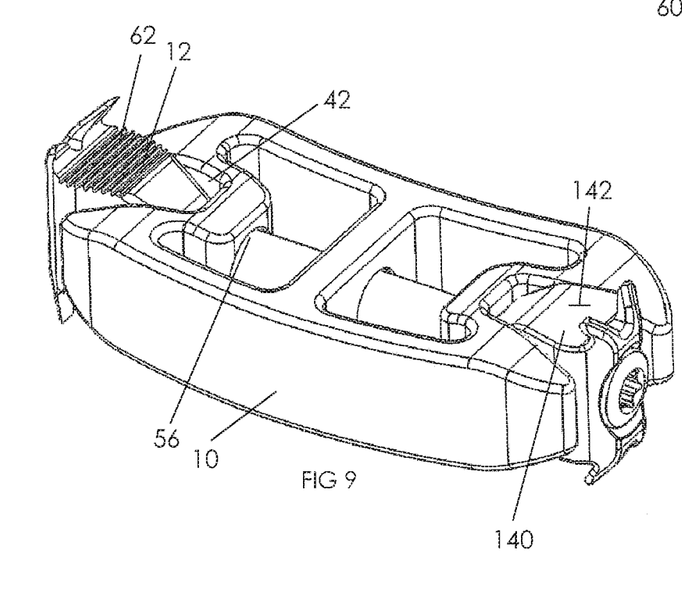
FIG. 9 is a perspective view of an alternative embodiment of the implant.

FIG. 8 depicts another embodiment with the bone tray 10 engaged to a distractor 12. In this embodiment, retainer member 130 includes a first wing 132 spaced apart from the retainer screw aperture 68 by a slot 124 to allow bone growth material to engage the retainer member. Similarly, wing member 126 is placed in line with wing member 132, having slot 128 for bone growth material. Retainer 16 is placed through the aperture 68 for engaging the distractor 12 for securing to the bone tray 10.

Referring now to FIGS. 9-13, the bone tray 10 may include distractor 12 to engage the receptacle 42 with a retainer 140 having a smooth surface 142, while an opposing distractor has a ridged surface 62. The distractor 12 may include spacing for receipt and movement of the retainer 16. Arrow 143 illustrates the movement of the retainer 16 which allows the distractor 12 to fit within the receptacle with a slight offset to accommodate uneven alignment during the distractor process.

Figure 14:
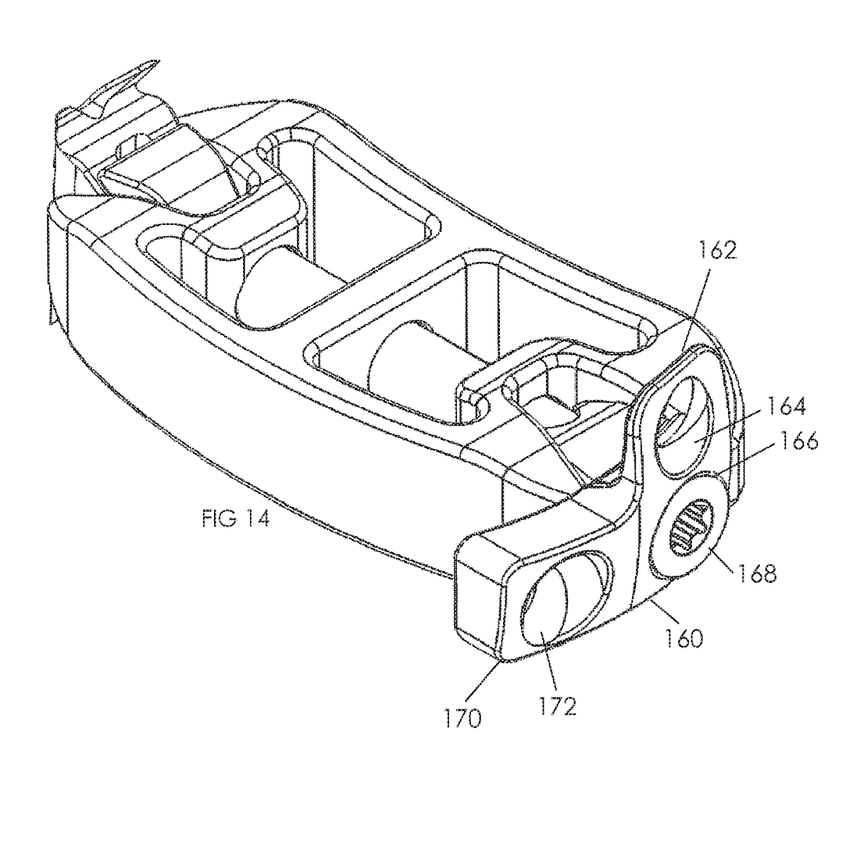
FIG. 14 is a perspective view of an alternative embodiment of the implant.
Figure 15:
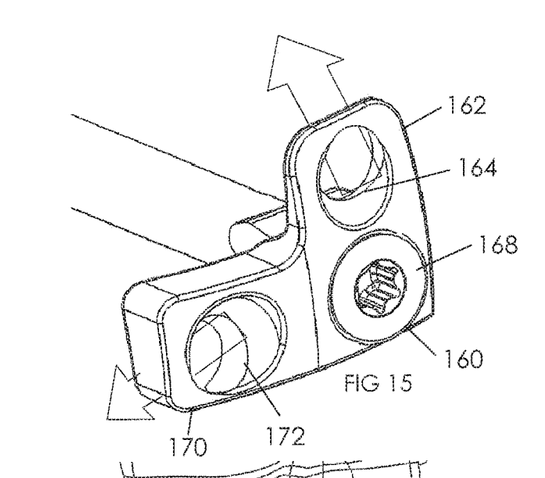
FIG. 15 is a perspective of the endplate.
Figure 16:
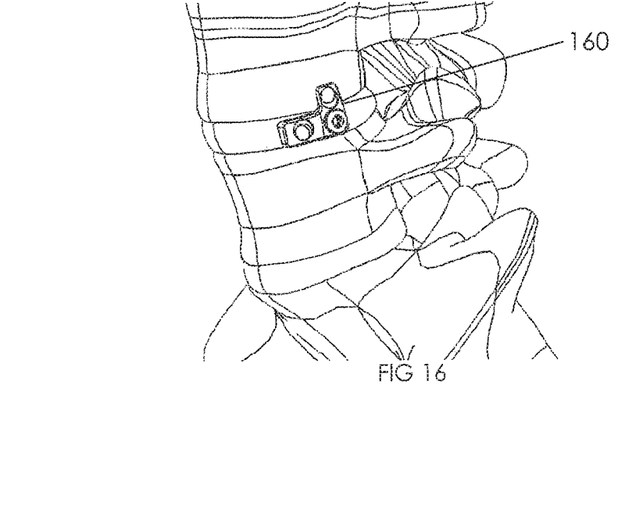
FIG. 16 is a pictorial view of the implant.

Referring now to FIGS. 14-16, illustrated is an embodiment using a retainer having a first wing 162 with aperture 164 placed in a perpendicular position to the retainer aperture 166 having retainer 168, with a second wing 170 offset with aperture 172. Apertures 164 and 172 for receipt of a mounting screw, not shown. Illustrated in FIG. 16 is the retainer 160 secured to a spinal disc.

All patents and publications mentioned in this specification are indicative of the levels of those skilled in the art to which the invention pertains. All patents and publications are herein incorporated by reference to the same extent as if each individual publication was specifically and individually indicated to be incorporated by reference.

It is to be understood that while a certain form of the invention is illustrated, it is not to be limited to the specific form or arrangement herein described and shown. It will be apparent to those skilled in the art that various changes may be made without departing from the scope of the invention and the invention is not to be considered limited to what is shown and described in the specification and any drawings/figures included herein.

One skilled in the art will readily appreciate that the present invention is well adapted to carry out the objectives and obtain the ends and advantages mentioned, as well as those inherent therein. The embodiments, methods, procedures and techniques described herein are presently representative of the preferred embodiments, are intended to be exemplary and are not intended as limitations on the scope. Changes therein and other uses will occur to those skilled in the art which are encompassed within the spirit of the invention and are defined by the scope of the appended claims. Although the invention has been described in connection with specific preferred embodiments, it should be understood that the invention as claimed should not be unduly limited to such specific embodiments. Indeed, various modifications of the described modes for carrying out the invention which are obvious to those skilled in the art are intended to be within the scope of the following claims.

What is claimed is:

1. A spinal implant for fusing adjacent vertebrae comprising:
   a bone tray having an open top side and an open bottom side adapted to engage adjacent vertebrae, a first sidewall connecting said top side and said bottom side separated from a second sidewall connecting said top side and said bottom side, said first and second sidewall having an equal thickness, said bone tray including at least one aperture extending from said top side to said bottom side for receipt of bone growth material;
   a distractor anchor having two sloped insertion walls with an aperture formed on said distractor anchor where said sloped insertion walls meet and an anchor member formed along an opposite portion of said distractor anchor, said distractor anchor having opposing end walls forming a width;

a retainer member operatively associated with said proximal end, said retainer member having a centrally disposed retainer member aperture and an engagement surface, said retainer member including a first wing mounted perpendicular to a second wing, each said wing having an aperture for receipt of a mounting screw; and a retainer screw insertable through said centrally disposed retainer aperture for coupling to said distractor anchor.

2. The spinal implant according to claim 1 wherein said anchor member is pivotally connected to the distractor anchor.

3. The spinal implant according to claim 1 wherein said distractor anchor sloped insertion walls are formed integral to said anchor member.

4. The spinal implant according to claim 1 wherein said distractor anchor is used as a retainer.

5. The spinal implant according to claim 1 wherein said distractor anchor comprises at least one barb extending outward from each end wall.

6. The spinal implant according to claim 1 wherein said distractor anchor end walls include teeth.

* * * * *